United States Patent
Troup et al.

(10) Patent No.: US 8,530,447 B2
(45) Date of Patent: Sep. 10, 2013

(54) DIETARY FIBER FORMULATION AND METHOD OF ADMINISTRATION

(75) Inventors: John P. Troup, Plymouth, MN (US); Anne L. Falk, Salt Lake City, UT (US)

(73) Assignee: Nestec S.A., Vevey (CH)

( * ) Notice: Subject to any disclaimer, the term of this patent is extended or adjusted under 35 U.S.C. 154(b) by 646 days.

(21) Appl. No.: 12/089,969

(22) PCT Filed: Oct. 23, 2006

(86) PCT No.: PCT/US2006/041568
§ 371 (c)(1),
(2), (4) Date: Sep. 12, 2008

(87) PCT Pub. No.: WO2007/050656
PCT Pub. Date: May 3, 2007

(65) Prior Publication Data
US 2010/0168056 A1     Jul. 1, 2010

Related U.S. Application Data

(60) Provisional application No. 60/742,124, filed on Dec. 2, 2005, provisional application No. 60/729,767, filed on Oct. 24, 2005.

(51) Int. Cl.
*A61K 31/715* (2006.01)
*A61P 1/00* (2006.01)
*A61P 3/10* (2006.01)
*A61P 9/12* (2006.01)

(52) U.S. Cl.
USPC ............................................................ 514/54

(58) Field of Classification Search
USPC ................................................................ 514/54
See application file for complete search history.

(56) References Cited

U.S. PATENT DOCUMENTS

| | | | |
|---|---|---|---|
| 6,203,797 | B1 | 3/2001 | Perry |
| 6,592,863 | B2 * | 7/2003 | Fuchs et al. ................ 424/93.1 |
| 2002/0132030 | A1 | 9/2002 | Michels et al. |
| 2004/0219157 | A1 | 11/2004 | Rochat et al. |

FOREIGN PATENT DOCUMENTS

| | | |
|---|---|---|
| EP | 1 243 273 | 9/2002 |
| EP | 1 386 546 | 2/2004 |
| WO | 99 42001 | 8/1999 |
| WO | 0060953 | 10/2000 |
| WO | 2004026294 | 4/2004 |
| WO | WO 2004/089115 A1 * | 10/2004 |
| WO | WO 2005/006891 | 1/2005 |
| WO | WO 2005/056023 | 6/2005 |

OTHER PUBLICATIONS

Tamura et al, J. Clin. Biochem. 1997, 23, 131-37.*
The Merck Manual 1992, pp. 110-112.*
Ide et al, Ann. Nutr. Metab. 1991, 35, 34-44.*
Truvill et al., "Cholera toxin-induced secretion in rats is reduced by a soluble fiber, gum arabic," Biosciences Information Service, vol. 45, No. 5, pp. 946-951, May 2000.
Canadian Office Action for Canadian Application No. 2,626,398 mailed Feb. 22, 2010.
Chinese Office Action for Chinese Application No. 200680039184.6 mailed Jan. 12, 2011. Considered only the English translation of this document provided.
Tamura, et al., "Effects of Guar Gum and Fructooligosaccharides on Plasma Lips and Cecal Short-Chain Fatty Acids in Adult Mice," J. Clin. Biochem, Nutr., 23, 131-137, 1997.
Ide, et al., "Hypolipidemic Effects of Guar Gum and Its Enzyme Hydrolysate in Rats Fed Highly Saturated Fat Diets," Ann Nutr Metab, 1991; 35:34-44.

* cited by examiner

*Primary Examiner* — Shaojia Anna Jiang
*Assistant Examiner* — Ganapathy Krishnan
(74) *Attorney, Agent, or Firm* — K&L Gates LLP

(57) ABSTRACT

The invention provides dietary fiber formulation and related methods for its administration. In one embodiment, the invention provides a dietary fiber formulation comprising: partially-hydrolyzed guar gum (PHGG); and fructooligosaccharides (FOS), wherein the dietary fiber formulation exhibits a prebiotic potential greater than a prebiotic potential of PHGG and FOS individually.

14 Claims, No Drawings

DIETARY FIBER FORMULATION AND METHOD OF ADMINISTRATION

CROSS REFERENCE TO RELATED APPLICATIONS

The present application is a National Stage of International Application No. PCT/US06/41568, filed on Oct. 23, 2006, which claims priority to U.S. Provisional Application 60/742,124, filed Dec. 2, 2005 and U.S. Provisional Application 60/729,767, filed Oct. 24, 2005, the entire contents of which are being incorporated herein by reference.

BACKGROUND OF THE INVENTION

1. Technical Field

The invention relates generally to dietary fibers and, more particularly, to a formulation including partially hydrolyzed guar gum (PHGG) and fructooligosaccharides (FOS), as well as methods for its administration.

2. Background Art

Dietary Fibers

Dietary fibers are carbohydrates derived primarily from plant cell walls that are resistant to digestion by human enzymes. They are well known for their ability to alter the intestinal milieu, thereby modulating physiological processes along the entire length of the intestine, with effects differing in the small and large intestine. The primary function of fiber in the small intestine is to enhance viscosity, while in the large intestine, it is to serve as a substrate for short-chain fatty acid (SCFA) production. The different physical properties of fibers and their corresponding effects collectively promote normal intestinal function.

Fibers are carbohydrates and lignin that cannot be hydrolyzed by human digestive enzymes but are fermented by intestinal bacteria to produce hydrogen, methane, carbon dioxide, water, and SCFA. Fibers are typically classified based on their fermentability, solubility, and viscosity. Most fermentable fibers are soluble and viscous, and most insoluble fibers are non-viscous and not completely fermentable. Currently, nutrition labeling focuses on solubility to classify the types of dietary fiber.

Insoluble fibers, including cellulose and lignin, are completely insoluble in water and are minimally fermented in the colon. They serve primarily as bulking agents, through their capacity to hold water. Insoluble fibers increase stool mass and promote the normal progression of contents through the intestine, attenuating constipation when liquid intake is adequate.

Soluble fibers dissolve in water and may be fermented by intestinal bacteria, 90% of which reside in the colon. Fermentability depends on the fiber's degree of solubility and particle size. For example, as the solubility of a fiber increases and its particle size decreases, it is more rapidly fermented. Soluble fibers impart various beneficial effects during digestion, such as delaying gastric emptying to extend the period of satiety, slowing the rate of glucose absorption, and binding sterol compounds to help lower elevated serum cholesterol. Soluble fibers include pectin, gums, some hemicelluloses, psyllium, guar gum, fructooligosaccharides (FOS), inulin, and galactooligosaccharides (GOS). In addition, significant amounts of soluble fiber are found in fruits, vegetables, and cereals, including barley and oats.

Additional beneficial effects of fiber are associated with their fermetability and production of SCFA. Acetate, propionate, and butyrate comprise 83% of the SCFA produced in the colon. SCFA are readily absorbed by intestinal epithelial cells, providing energy and stimulating sodium transport, water absorption, and intestinal growth. Through these mechanisms, SCFA help normalize loose, watery stools brought on by prescription drugs, exposure to pathogenic bacteria, and illness. Furthermore, as the preferred fuel for colonic mucosal cells, butyrate has a critical role in influencing the normal growth and development of colonic epithelial cells. Accordingly, butyrate possesses anti-cancer activity and contributes to mucosal integrity. Respectively, these properties help the body defend itself from malignant progression and pathogenic bacterial invasion.

Physiologically, SCFA are at low concentrations in the ileum. However, the level of ileal SCFA may increase in some physiological and clinical conditions. Numerous studies have demonstrated that SCFA present in the terminal ileum stimulate peristaltic contractions and increase tonic activity, which may elicit an emptying response. Accordingly, fibers that produce high amounts of SCFA can increase intestinal motility and potentially alleviate constipation.

SCFA concentrations are highest in the proximal large intestine, mainly because of greater carbohydrate availability. In vitro fermentation experiments with fecal bacteria have demonstrated that individual polysaccharides are broken down at different rates. This finding is relevant to bacterial catabolic processes in the gut because, to a large extent, substrate concentration regulates the way in which the organisms compete for fermentable substrate as well as the control mechanism involved in fermentation reactions.

Studies have shown that the type of fiber present in the diet will influence not only the amount, but also the proportion, of the SCFA produced during fermentation. Acetate production appears to originate mainly from the fermentation by glycolytic colonic bacteria and the fructose-6-phosphate phosphoketolase shunt of bifidobacteria. Propionate originates mainly from carbon dioxide fixation of *bacteriodes*, and butyrate originates primarily from acetyl-S coenzyme A condensation of *fusobacterium* and *eubacterium*.

One study has reported that the highest acetate production was from glucose fermentation, followed by FOS fermentation. This is likely the result of glycolysis and the bifidobacteria shunt, respectively. High propionate production has been achieved from cellulose and PHGG fermentation, and high butyrate levels were obtained through the fermentation of psyllium husk and PHGG. Partially-hydrolyzed guar gum (PHGG) produced the greatest amount of SCFA after 24 hours of batch culture.

Growth of Microbiota

SCFA promote a healthy gut environment by stimulating the growth of beneficial bacteria, such as bifidobacteria and lactobacilli, and inhibiting the growth of harmful bacterial strains. Beneficial bacteria promote intestinal health by stimulating a positive immune response and out-competing the growth of harmful bacteria. It is for these reasons that SCFA are so important following radiation therapy, the use of antibiotics, extreme changes in diet, and other events known to upset microbiota subpopulations in the intestine. In association with cultivating a positive microbiota, soluble fibers have a mild laxative effect that can help prevent or alleviate constipation.

The human intestinal tract can be thought of as an ecosystem where bacterial subpopulations from about 800 species of bacteria interact with one another, host intestinal epithelial cells, and components of the host immune system. Specific bacterial subpopulations flourish when the intestinal environment is suitable. Nutrient availability, pH, physiological processes, and the absence of competing bacteria all affect the mix of bacteria that colonize the gut at a given time.

Beneficial bacteria, generally referred to as probiotics, have been used for years to increase the proportion of beneficial bacteria in the intestine and to prevent or treat medical conditions. Beneficial effects attributed to probiotics include lesser frequency and shorter duration of diarrhea associated with antibiotics and chemotherapy, stimulation of positive immune response, and reduction of cancer-promoting enzymes in the colon. For a probiotic to promote the growth of beneficial bacteria in the intestine, it must survive passage through the stomach and retain its ability to colonize in the distal intestine and colon. Commonly used probiotics include strains of lactobacilli and bifidobacteria. Common food sources of probiotics are yogurt, buttermilk, kimchi, sauerkraut, and other cultivated and fermented foods.

Prebiotics are growth substrates for potentially beneficial bacteria present in the colon. For example, beneficial bacteria supported by prebiotics help to maintain mucosal growth and function, including the transport of water and electrolytes. Thus, prebiotics have been defined as non-digestible food ingredients that affect a host beneficially by selectively stimulating the growth and/or activity of one or a limited number of bacteria known to improve health. However, under this definition, prebiotic use is predicted, at least partially, on the expectation that there is a defect in the host's microbiota and that the provision of prebiotics would be beneficial. This definition also implies that a prebiotic acts to stimulate the growth of organisms within the large bowel alone. However, bacteria are also present in the terminal ileum and prebiotics can stimulate the growth of these organisms, also improving the health of a host.

Synbiotics are a mixture of pre- and probiotics that beneficially affect the host. This combination improves probiotic survival during passage through the upper gastrointestinal tract and promotes more efficient colonization within the colon. Thus, synbiotics may have the same net effect as a prebiotic, i.e., the growth of beneficial bacteria in the colon. Synbiotics administered to tube fed patients following major abdominal surgery or liver transplantation have been shown to decrease the incidence of postoperative infections in comparison with parenteral nutrition or fiber-free tube feedings.

Immunomodulatory and Antiinflammatory Effects

The inter-relationship between enteric flora, innate immunity, and the mucosal immune system is believed to play a critical role in health and the pathophysiology underlying the chronic destructive inflammation that, characterizes inflammatory bowel disease (IBD). Normally, enteric colonic bacteria will not induce a destructive inflammatory response in the gut. In fact, products of bacterial fermentation are known to play an active and beneficial role in epithelial and colonic homeostasis. SCFA derived from enteric bacterial fermentation of non-digested dietary carbohydrates provides an essential energy substrate for the colonic epithelium. A deficiency of SCFA may result in the development of colitis, a chronic gut inflammation.

One study reported that butyrate alters the gene and protein expression of intracellular cell adhesion molecule-1 (ICAM-1), IL-6, COX-2, and PGE2 in human intestinal microvascular endothelial cells in response to bacterial lipolysaccharide. This indicates an immunomodulatory and anti-angiogenic role for butyrate.

Butyrate has also been reported to inhibit TNF-α stimulated expression of vascular cell adhesion molecule-1 (VCAM-1) and ICAM-1 in human umbilical vein endothelial cells (HUVEC) by reducing both protein and specific mRNA production through inhibition of NF-KB activation. In addition, butyrate is known to enhance peroxisome proliferators-activated receptor-α (PPAR-α). These results demonstrate that butyrate may have anti-inflammatory properties not only in colonocytes, but also in endothelial cells. The anti-inflammatory and anti-atherogenic properties of butyrate may partly be attributed to an affect on activation of NF-KB and PPAR-α and to the associated expression of VCAM-1 and ICAM-1.

Butyrate Transport

Recently, specific G-protein-coupled receptors have been identified for SCFA in mammals, expressed predominantly on the plasma membrane of immune cells. Gut-associated immune cells present the lamina propria just under the epithelial cell layer. The concentration of SCFA needed to activate these receptors is between about 0.01 mM and about 1.0 mM. Because the luminal concentrations of SFCA are quite high in the colon, SCFA are likely to reach such concentrations on the serosal side of the colonic epithelial cell layer, aided by their absorption via sodium-coupled monocarboxylate transporter (SMCT). Therefore, these receptors have relevance to various physiological and pathological conditions related to intestinal inflammation and anti-tumor immunity. The ability of the transporter to mediate active absorption of butyrate, an inhibitor of histone deacetylases, may underlie its tumor suppressive role in the colon.

SCFA also serve as ligands for specific G-protein-coupled receptors on gut-associated immune cells. Since concentrations of these fatty acids in the colonic lumen are quite high, SMCT may facilitate transcellular transfer of these fatty acids from the lumen into the lamina propria, where immune cells reside, thus providing a link between gut flora and the gut immune system.

Several studies have shown that treatment with butyrate upregulates various transcription factors, such as PPAR-γ, as well as vitamin D receptor mRNA and protein levels. Another study showed that butyrate influences PPAR-γ expression, but does not directly activate this receptor. PPAR-γ is a nuclear receptor that controls the expression of a large array of genes involved with adipocyte differentiation, lipid metabolism, insulin sensitivity, inflammation, and atherogensis. Thus, fibers that are preferentially fermented by microbes that produce butyrate may have a beneficial role in treating diabetes, cardiovascular diseases, and inflammatory bowel disease.

Prebiotic Potential

Dietary fibers classified as prebiotics can modulate the growth of bacterial subpopulations and, when combined with exogenous beneficial bacteria or probiotics, are defined as synbiotics, capable of further supporting digestive health. Soluble fibers may have high, moderate, or low prebiotic potential, depending on their ability to stimulate growth of beneficial bacteria, their length of fermentation time, and the amount of SCFA they produce. Insoluble fibers have little or no prebiotic effect, as they are only minimally fermented by bacteria in the colon.

Quantitative in vitro methods are known for measuring the prebiotic effect of a fiber. The measurable effect a fiber has on the growth of major bacterial species in the human gut, bifidobacteria and lactobacilli in particular, is the measure of the prebiotic effect (MPE). MPE has three components:

1. the rate fiber is fermented;
2. the changes in bacterial populations; and
3. the production of SCFA.

The rate of fiber fermentation is determined by the change in the concentration of fiber over time. Thus, the quicker the fiber concentration decreases, the faster the rate of fermentation by bacteria. Changes in bacterial populations are measured by the "prebiotic index," which considers increases in the growth rate of bifidobacteria, lactobacilli, and eubacteria as positive effects and increases in *bacteriodes*, clostridia, *Escherichia coli*, and sulphate-reducing bacteria as negative effects. Different fibers support the growth of distinct bacteria and therefore yield varying patterns and/or amounts of SCFA. However, the prebiotic effect is usually associated with lactic acid-producing bacteria, bifidobacteria and lactobacilli being principle lactic acid producers. Therefore, the ratio of lactic acid production relative to the total SCFA production provides a qualitative as well as quantitative assessment of the fibers being examined. The MPE provides a quantitative analysis of the prebiotic potential of a fiber and provides further support for the benefits of specific fibers. Therefore, the MPE is a useful tool in identifying the types and specific amounts of fiber that promote optimal digestive health and prevent or treat intestinal diseases.

The balance between beneficial and pathogenic bacteria is extremely important for the maintenance of normal intestinal physiology, as this balance has direct effects on immune function and nutrient digestion and absorption. Select fibers offer additional benefits to digestive health, derived from their ability to influence intestinal bacterial subpopulations. In this manner, dietary fiber indirectly contributes to:

- an improvement in mucosal barrier function, preventing the transit of pathogenic bacteria from the intestine to the bloodstream;
- the promotion of beneficial subpopulations and reduction of pathogenic bacterial subpopulations;
- the production of SCFA, the major energy source for epithelial cells in the large intestine; and
- an improvement in host immunity, via interactions between intestinal immune cells and pathogenic bacteria.

The unique chemical, biological, and physical properties of dietary fiber are responsible for the health benefits associated with its consumption. Ample intake of fiber is recommended for good health of the general population, as a high fiber diet can help prevent and treat a variety of chronic conditions that affect the digestive system, as well as other systems of the body. For example, dietary fiber has normalizing effects on elevated blood pressure and cholesterol levels and is associated with reduced risk of cardiovascular disease. Moreover, dietary fiber is especially important in the care of pediatric and geriatric populations as well as post-surgical, critically- and chronically-ill patients.

For example, in post-surgical and critically-ill patients, as well as those requiring enteral nutrition for an acute period, soluble fiber helps prevent diarrhea, frequently associated with enteral feedings. For patients with impaired gut function, administration of 6 to 10 g of fiber per liter is appropriate. Clinical trials have shown that post-surgical patients and patients with normal gut function benefit from higher fiber intakes, 10 to 15 g per liter being an appropriate supplement. Following major abdominal surgery or liver transplantation, the incidence of postoperative infections has been shown to be significantly lower in patients whose enteral formula was supplemented with a blend of fiber and an accompanying probiotic, while outcomes were not as favorable in patients receiving the conventional fiber-free formula.

For patients with chronic illness or disease and those requiring enteral nutrition for a long-term period, intake of both insoluble and soluble fibers is appropriate. Constipation is a frequent problem in these patients, often due to immobility, advanced age, or inadequate fluid and/or fiber intake. Constipation is especially common in tube-fed patients. Inclusion of a blend of fibers at intakes recommended for the general population, if tolerated, can help to prevent constipation and the need to rely on laxatives and enemas. The prebiotic effect of soluble fibers, alone or in combination with a probiotic, may help to alleviate or prevent antibiotic-associated or infectious diarrhea in chronically-ill patients as well.

Dietary Recommendations

Diets scarce in fiber are associated with an increased risk for disease. In contrast, high fiber diets can normalize or improve digestive health. A fiber-rich diet that includes both soluble and insoluble fibers is encouraged. Recommended daily intakes of fiber are 20 to 35 g for healthy adults. Recommended daily intakes for children are calculated by adding the child's age and adding 5 g, for children age 2 years and older. Average fiber intake continues to be below recommended levels in the US, with typical intakes averaging only 14 to 15 g per day. Good sources of dietary fiber include fruits and vegetables, whole- and high-fiber grain products and legumes. High intake of these foods on a habitual basis is generally uncommon. Furthermore, many of the foods popular in the Western diet contain little dietary fiber. Even individuals who consume a fiber-rich diet may have inadequate fiber intake to prevent constipation. Therefore, supplementation is important under these circumstances.

A diet rich in fiber is associated with the prevention and treatment of disease, including obesity, metabolic syndrome, heart disease, stroke, diabetes, colon cancer, and digestive disorders. Understanding of how fiber interacts with the intestinal milieu to promote health and/or treat disease ranges from early stages, where an association has been identified, to further stages, where mechanisms have been hypothesized.

Obesity

Evidence suggests that ample intake of dietary fiber can help prevent weight gain and promote weight loss. Suggested modes of action include the slowed gastric emptying that extends postprandial satiety and leads to improved glucose control following meals high in fiber. Epidemiological studies have identified that adults with diets higher in fiber tend to be leaner and are less likely to be obese than adults with low fiber intakes. In clinical trials, an additional 14 g of fiber per day resulted in a 10% decrease in energy intake and a weight loss averaging 1.9 kg over four months.

Heart Disease and Stroke

Numerous clinical trials have reported that increased intakes of viscous fibers decrease total and low-density lipoprotein (LDL) cholesterol, leading to the United States Food and Drug Administration approved health claim: "Soluble fiber from foods such as oat bran, as part of a diet low in saturated fat and cholesterol, may reduce the risk of heart disease." In addition, a pooled analysis of 10 prospective cohort studies of fiber intake in the United States and Europe found that each 10 g per day increase in fiber was associated with a 14% decrease in the risk of coronary events and a 24% decrease in deaths from coronary heart disease. Diets rich in fiber may also help reduce elevated blood pressure levels. Two intervention trials found that increasing fiber intake from oat cereals and oat bran resulted in modest but significant improvements in hypertension. While dietary and supplemental intake of viscous fibers are effective in lowering LDL cholesterol, large epidemiological studies provide strong evidence that diets rich in fiber from whole grains, legumes, fruits, and vegetables can reduce coronary heart disease risk as well.

Diabetes

Several prospective cohort studies have found that diets rich in fiber are associated with significant reductions in the risk of developing type 2 diabetes. Fiber consumption, whether from foods or supplements, has been shown to have a beneficial effect on blood glucose and insulin responses, as well as lipid profiles. The results of 23 clinical trials found that high fiber diets lowered postprandial glucose levels by between 13 and 21%, LDL cholesterol levels by between 8 and 16%, and triglyceride levels by between 8 and 13%. Based on this, the American Diabetes Association recognizes the benefits dietary fiber provides the diabetic population, as reflected in their recent recommendation for consumption of at least 25 to 50 g of fiber per day.

Metabolic Syndrome

Metabolic syndrome is an emerging disease condition in adults. It is medically defined as the clustering of three or more of the following biological risk factors: abdominal obesity, insulin resistance, dyslipidemia (high triglycerides and low high-density lipoprotein (HDL) cholesterol), and elevated blood pressure. In the presence of metabolic syndrome, the risk for cardiovascular disease and diabetes rise dramatically. A recent epidemiological study identified that in an eight-year period, 20% of all cardiovascular events and over 50% of new cases of diabetes occurred in individuals with metabolic syndrome. While more than 20% of the US population has metabolic syndrome, risk is associated with several modifiable lifestyle factors, including dietary fiber intake. For example, in a group of more than 1500 women, aged 40 to 60 years, the risk for metabolic syndrome was significantly greater in the group that consumed the lowest intakes of dietary fiber, averaging 14.6 g of fiber for every 2000 kilocalories consumed and meeting approximately half of the recommended daily intake. Overall, habitual dietary patterns were identified that included higher intakes of fat, kilocalories, and sweetened beverages, as well as the lowest intakes of vegetables and dietary fiber. Identification of at-risk individuals, clinical management, and targeted behavior change, including nutrition intervention with a diet high in fiber, are vital for the prevention of metabolic syndrome and its potential comorbidities.

Colon Cancer

The majority of clinical trials conducted prior to 1990 found the incidence of colorectal cancer was reduced in people with higher fiber intakes. Evidence suggests that dietary fiber, especially soluble and fermentable sources of fiber, act to prevent the formation of toxins that may initiate cancer and hasten their excretion. In addition, SCFA produced by fiber fermentation promote colonic epithelial growth, regress tumors via a positive immune response pathway, and modulate gene expression towards an anti-cancer phenotype. However, more recent trials have not found significant associations between fiber intake and colorectal cancer risk. A possible reason for these discrepancies may be that the current classification system does not adequately identify variations in specific types and amounts of fiber that are associated with anti-cancer effects. Another possibility is that certain dietary components may interact with fiber to influence its effect on cancer initiation.

Digestive Disorders

Fiber plays a crucial role in general intestinal health. It has an overall normalizing effect on the digestive system. Increasing intake of fiber to meet recommendations prevents or ameliorates constipation by softening, adding bulk, and speeding the passage of contents through the intestinal tract. Fiber also prevents and treats diarrhea, which is of special importance to the pediatric and geriatric populations and critically- and chronically-ill patients. In addition, fiber plays a key role in the prevention and management of various digestive disorders associated with inflammation, as described above. High fiber intakes are associated with a decreased risk of diverticulosis, a condition characterized by the formation of small pouches in the colon. One study found that men with a high fiber intake had a 42% lower risk of developing diverticulitis. A recent review of patients with irritable bowel syndrome (IBS) demonstrated significant improvements in IBS symptoms with soluble fiber supplementation. However, improvements were not observed with dietary supplementation of insoluble fibers. Furthermore, remission was induced in patients with ulcerative colitis through a synbiotic treatment. In summary, soluble fiber can be beneficial not only for healthy individuals to aid in the maintenance of digestive health, but also for individuals with impaired digestive function or health due to illness or disease.

Cholera

In cholera, small intestinal function is affected involving stimulation of secretory process and reduction in absorption of water and electrolytes from small and large intestine in response to cholera toxin. Profuse watery diarrhea needs immediate rehydration therapy or death can result.

The human colon has the capacity to absorb water and electrolyte and absorption is increased in the presence of SCFAs. SCFAs also inhibit c-AMP mediated chloride secretion in the colon. Partially hydrolyzed guar gum (PHGG) (Benefiber) is a water-soluble fiber and if added to oral rehydration solution (a WHO recommended ORS containing having no other overt fiber content) (ORS) undergoes fermentation in the colon liberating SCFAs. SCFAs stimulate water and sodium absorption in the colon thus reducing the severity of diarrhea by reducing the stool output and duration of diarrhea in the treatment of cholera patients.

In an open randomized controlled trial 130 male adult cholera patients were studied; 65 received a) ORS+25 g of Benefiber; b) 65 received ORS alone (control). All patients received doxycycline 300 mg once.

Results: Baseline clinical characteristics were comparable between the groups. No significant differences were found in stool wt (g) during $1^{st}$ 24 h, mean±SD (Benefiber 25 g, 10206±5770 vs. control group, 10231±3750), $2^{nd}$ 24 h (Benefiber 25 g, 2418±3472 vs. control group 2172±3931 p=0.708) Duration of diarrhea (h) after admission in hospital was also similar in both groups (Benefiber 25 g, 31.4±11.1 vs. control group, 32±12.5). However, in a subgroup analysis (excluding very high purging patients, stool weight $1^{st}$ 24 h>10 kg), the stool weight was significantly reduced in $1^{st}$ 24 h in the Benefiber receiving group (Benefiber 25 g, 5940±2920 vs. control 7913±1515, p=0.001). Benefiber added to WHO recommended ORS is beneficial in reducing the stool weight in less severely purging patients.

Cholera II

Partially hydrolyzed guar gum is a water-soluble fiber and if added to oral rehydration solution containing or supplemented with at least one more water-soluble fiber, preferably 2 or less additional fiber sources, more preferably 1 additional fiber source, such as pectin, gums, some hemicelluloses, psyllium, other guar gum, fructooligosaccharides (FOS), inulin, and galactooligosaccharides (GOS), preferably FOS or inulin, more preferably inulin, the fibers should undergo fermentation in the colon liberating SCFAs reducing the severity of diarrhea by reducing the stool output and duration of diarrhea in the treatment of cholera patients much more than Benefiber alone.

Partially-Hydrolyzed Guar Gum and Fructooligosaccharides

Two types of fiber, partially-hydrolyzed guar gum (PHGG) (such as is sold by Novartis under the name Benefiber) and fructooligosaccharides (FOS), have been extensively studied. Each has been shown to promote digestive health.

PHGG is a unique, soluble, functional fiber extracted from guar gum. The original high viscosity of guar gum is nearly eliminated after hydrolysis, making it an ideal addition to liquid foods and nutritional formulas.

Many of the beneficial effects of PHGG are likely due to the fact that it is almost completely fermented in the colon and that it produces significantly more butyrate than other soluble fibers. Butyrate is known to be the preferred fuel for colonocytes and plays a role in the regulation of cell proliferation, differentiation, and apoptosis in the intestine. Like other soluble fibers that are rapidly fermented in the proximal colon, PHGG does not significantly increase stool weight. However, a number of studies have shown that PHGG is beneficial in normalizing bowel function, as well as preventing or alleviating both diarrhea and constipation, especially in patients receiving enteral nutrition and other populations sensitive to intestinal intolerance.

In one study children aged 4 to 18 months suffering from acute watery diarrhea for less than 48 hours, experienced decreased stool output and duration of diarrhea following the consumption of an oral rehydration solution supplemented with PHGG. In another study, the addition of PHGG to a chicken-based formula enhanced recovery from diarrhea in children, aged 5 to 24 months, with a history of watery diarrhea persisting for more than 14 days.

PHGG supplementation has also been shown to decrease the incidence of diarrhea in elderly, tube-fed patients, when compared to a conventional fiber-free formula. In one study, none of the patients receiving PHGG supplementation (20 g per day) experienced intolerance, while four of the patients receiving the fiber-free formula had persistent diarrhea that necessitated discontinuation of the tube feeding. In another study, the incremental supplementation of PHGG to a standard enteral formula (starting with 7 g per day, increasing to 28 g per day by week 4) significantly decreased stool frequency in elderly patients, increased the production of SCFA, and normalized the balance of gut bacteria. PHGG supplementation (22 g per liter) reduced diarrhea in other enterally-fed patient groups as well. In addition, diarrheal episodes were reduced in fully-resuscitated and mechanically-ventilated septic patients and intensive care unit patients with persistent diarrhea.

PHGG also effectively normalizes constipation. In one study, long-term care residents with constipation managed by enemas who received daily PHGG supplementation (18 g) had significantly decreased enema requirements, especially in residents with higher initial enema usage. In another study, PHGG supplementation (15 g per day) reduced constipation and laxative management in long-term care residents with chronic laxative use. PHGG supplementation has also been shown to shorten the interval between bowel movements in women with constipation (PHGG supplementation of 11 g per day), effectively normalize bowel movements in adults with IBS, and improve symptoms of abdominal pain and bowel irregularity compared to subjects who received wheat bran (PHGG supplementation of 5 g per day).

PHGG is considered a prebiotic, as it increases the concentration of the beneficial bacterial strains bifidobacteria and lactobacilli. One study has shown that bifidobacteria increased 17% in healthy subjects consuming a diet containing PHGG (21 g per day) for two weeks. Augmented growth of lactobacilli was also detected. Others have reported consistent findings, detecting significant increases in lactobacilli following daily supplemental intakes of PHGG of 8 g per day.

Fructooligosaccharides (FOS) are short-chain fructose polymers often compared to inulin, which is a longer-chain fructose polymer. Several plants are natural sources of FOS, including chicory, artichokes, asparagus, and onion. A number of methods of producing or obtaining FOS are known, including, for example, synthesis from sucrose, hydrolysis of inulin, extraction from chickory root, extraction from Jerusalem artichoke, and extraction from Agave. A highly fermentable fiber with prebiotic activity, FOS stimulates the growth of bifidobacteria and lactobacilli. Like PHGG, studies have shown that FOS can prevent or alleviate constipation and diarrhea.

By encouraging the growth of bifidobacteria, FOS promotes intestinal health, enhancing a positive immune response and suppressing the growth of pathogenic bacteria that may cause diarrhea. One study reported that adding 4 g per day of FOS to the diets of healthy adults increased bifidobacteria in just under a month. Other studies have detected significant increases in both bifidobacteria and lactobacilli within 14 days of dietary FOS supplementation of 4 g per day. In addition, it has been shown that FOS, administered at 15 g per day, not only increases bifidobacteria within 15 days of intake, but also decreases levels of pathogenic bacteria, specifically *bacterioides, clostridia, and fusobacteria*.

By promoting a positive microbial balance, FOS enhances intestinal regularity. In a multicenter trial of children receiving antibiotic therapy, a synbiotic combination of FOS and lactobacilli decreased the incidence of diarrhea. In the FOS+ lactobacilli supplementation group, 71% of the children experienced no tolerance problems, while 38% of the children in the placebo group experienced diarrhea. The duration of diarrheal episodes was significantly decreased in the FOS+ lactobacilli supplementation group. In that group, diarrhea lasted for 0.7 days, on average, versus an average of 1.6 days in the placebo group. Another study showed that when FOS was administered to constipated patients for 28 days, irregularity was relieved in 73% of the patients. Similarly, in a study of dialysis patients, a renal formula with added FOS lessened constipation, when compared to a similar formula without FOS.

While the studies above demonstrate a role for dietary fiber in the maintenance and improvement of a host's health, a need exists for dietary fiber formulations and methods for their administration that provide health benefits not provided or greater than those provided by known formulations and methods. In particular, there is a need for dietary fiber formulations that more fully realize the prebiotic potential of dietary fiber.

SUMMARY OF THE INVENTION

The invention provides a dietary fiber formulation and related methods of administration. In one embodiment, the invention provides a dietary fiber formulation comprising: partially-hydrolyzed guar gum (PHGG); and fructooligosaccharides (FOS), wherein the dietary fiber formulation exhibits a prebiotic potential greater than a prebiotic potential of PHGG and FOS individually.

A first aspect of the invention provides a dietary fiber formulation comprising: a first soluble fiber; and a second soluble fiber, wherein the dietary fiber formulation exhibits a prebiotic potential greater than a prebiotic potential of the first soluble fiber and the second soluble fiber individually.

A second aspect of the invention provides a method of treating an individual with a dietary fiber formulation, the method comprising: administering to the individual an effective amount of a dietary fiber formulation comprising: a first soluble fiber; and a second soluble fiber, wherein the dietary fiber formulation exhibits a prebiotic potential greater than a prebiotic potential of the first soluble fiber and the second soluble fiber individually.

The illustrative aspects of the present invention are designed to solve the problems herein described and other problems not discussed, which are discoverable by a skilled artisan.

DETAILED DESCRIPTION

As indicated above, the invention provides a dietary fiber formulation and related methods of administration. The formulations of the present invention may be administered, for example, to treat an individual suffering from any of a number of diseases or medical conditions, including irritable bowel syndrome (IBS), inflammatory bowel disease (IBD), diarrhea, constipation, diabetes, hypertension, dyslipidemia, obesity, heart disease, and stroke. Similarly, a formulation of the present invention may be administered to promote the growth of beneficial bacteria in a host's intestinal environment, thereby preventing or reducing the likelihood that the host will suffer from such a disease or medical condition.

As used herein, the terms "treatment" and "treat" refer to both prophylactic or preventive treatment and curative or disease-modifying treatment, including treatment of patients at risk of contracting a disease or suspected to have contracted a disease, as well as patients who are ill or have been diagnosed as suffering from a disease or medical condition. Consequently, an "effective amount" is an amount that treats a disease or medical condition in an individual.

Surprisingly, it has been found that a combination of fructooligosaccharides (FOS) and partially-hydrolyzed guar gum (PHGG) has a greater prebiotic effect on gut health than either has when administered alone. Due, in part, to the fact that each fiber has a distinct fermentation rate and specific intestinal regions of activity, a PHGG/FOS blend has a lengthened fermentation time in the intestinal tract and produces a greater variety of short-chain fatty acids (SCFAs), particularly acetate, propionate, and butyrate, than exhibited by either fiber individually. A comparison of fermentation times, SCFA productions, and prebiotic potentials of PHGG, FOS, and a PHGG/FOS blend according to the present invention is shown in Table 1.

TABLE 1

Comparative Benefits of Individual and Blended Fibers

|  | PHGG | FOS | PHGG and FOS Blend |
|---|---|---|---|
| Fermentation Time | 1 | 0.5 | 1 |
| SCFA Production | 1.27 | 0.46 | 1 |
| Prebiotic Potential | 0 | 0.67 | 1 |
| Total | 2.27 | 1.63 | 3 |
| Relative Source | 76% | 54% | 100% |

Overall, these results show a 24% greater benefit in the PHGG/FOS blend compared to PHGG alone and a 46% greater benefit in the blend compared to FOS alone. In particular, it is noted that the prebiotic potential of the blend is significantly higher than the prebiotic potentials of PHGG or FOS alone.

Table 2 shows the broader benefit of the PHGG/FOS blend of the present invention compared to individual fibers and fiber blends, as evidenced by their calculated measure of prebiotic effect (MPE) values. Each value is based on stirred, pH-controlled batch culture fermentations using 0.25%, 0.5%, and 1.0% (w/v) substrates in the presence of human fecal bacteria.

TABLE 2

Comparative MPE Values for Fibers and Fiber Blends

|  | MPE | | |
|---|---|---|---|
|  | 0.25% | 0.5% | 1% |
| Sucrose | −0.3 | −0.3 | −0.6 |
| Guar Gum | −0.2 | −0.3 | −0.4 |
| Sunfiber | — | — | −0.2 |
| Benefiber (PHGG) | −0.04 | −0.1 | −0.1 |
| isomaltooligosaccharides | −0.1 | −0.1 | 0.1 |
| FOS:Benefiber (90:10) | −0.04 | 0.1 | 0.2 |
| TOS:Benefiber (90:10) | 0.05 | 0.1 | 0.2 |
| SOS | −0.1 | −0.1 | 0.3 |
| FOS | −0.1 | 0.1 | 0.4 |
| Trans-galactooligosaccharides (TOS) | 0.1 | 0.2 | 1.0 |
| FOS:TOS (50:50) | 0.3 | 0.4 | 1.4 |

While Table 2 indicates that at 1% substrate, FOS has a greater MPE than the FOS:PHGG blend, it is noted that the in vivo effects of FOS alone occur primarily in the distal small intestine and proximal colon, where its beneficial effects could not be fully utilized by the body. By contrast, the in vivo effects of the FOS:PHGG blend occur primarily in more distal portions of the colon.

When the prebiotic potentials of FOS and PHGG were evaluated in vitro, a blend of the two fibers enhanced the growth of the beneficial bacterial strains bifidobacteria and lactobacilli to a degree greater than or equivalent to either fiber alone. When the prebiotic potential was evaluated using a crossover study design, administration of 6.6 g of FOS and 3.4 g of PHGG per day for 21 days significantly increased bifidobacteria, compared to initial levels or those achieved following a 21 day placebo period. Bifidobacteria levels returned to pretreatment levels seven days after the FOS and PHGG blend supplementation was discontinued. Volunteers with the lowest initial levels of the beneficial bacteria achieved the greatest total increase.

A blend of FOS and PHGG according to the present invention combines the prebiotic activity of FOS with the high butyrate productivity of PHGG. Table 3 summarizes the unique attributes of the blend compared to other fibers. The combination of FOS and PHGG enhances the level of SCFA, particularly butyrate, provides a strong prebiotic benefit, promoting both intestinal health and the growth of beneficial bacteria, and increases fermentation activity over a greater length of the intestine. Therefore, the blend of FOS and PHGG maximizes or exceeds the individual effects of each fiber and provides optimal benefits for intestinal health and function.

TABLE 3

Attributes of Dietary Fibers

|  | PHGG | FOS | PHGG and FOS Blend | Psyllium | Soy Fiber | Inulin | Oat Fiber |
|---|---|---|---|---|---|---|---|
| Rate of Fermentation | Slow | Fast | Slow | Very slow | Very slow | Moderate | Very slow |
| Degree of Fermentation | High | High | High | Moderate | Moderate | High | Moderate |

TABLE 3-continued

Attributes of Dietary Fibers

|  | PHGG | FOS | PHGG and FOS Blend | Psyllium | Soy Fiber | Inulin | Oat Fiber |
|---|---|---|---|---|---|---|---|
| Effect on SCFA Concentration | Moderate production of butyrate | Low production of all SCFA | Moderate production of butyrate | Low production of all SCFA | Low production of all SCFA | Low production of all SCFA | Low production of all SCFA |
| Effect on Gut Barrier Region of Benefit | Some, protective Proximal to mid colon | Some, protective Distal small intestine to proximal colon | Some, protective Distal small intestine to mid colon | Some, protective Proximal to distal colon | Some, protective Proximal to distal colon | Some, protective Proximal to mid colon | Some, protective Proximal to distal colon |
| Degree of Microfloral Stimulation/ Prebiotic Potential | Low stimulation of microflora | Moderate stimulation of bifidobacteria and limited stimulation of lactobacilli | Moderate stimulation of microflora | Low stimulation of microflora | Low-to-moderate stimulation of microflora | Low stimulation of microflora | Low stimulation of microflora |
| Effect on Negative Microflora | Low inhibition | Moderate inhibition | Moderate inhibition | Low inhibition | Low inhibition | Low inhibition | Low inhibition |
| Taste and Texture | Excellent | Excellent | Excellent | Poor | Poor | Good | Poor |
| Effect on GI Regularity (Type of Evidence) | Promotes (multiple clinical studies) | Promotes (clinical studies) | Promotes (exp. evidence, clinicals underway) | Promotes (clinical studies) | Promotes (clinical studies) | Promotes (clinical studies) | Promotes (clinical studies) |

The FOS/PHGG blend of the present invention is particularly beneficial for individuals suffering from inflammatory bowel disease (IBD). IBD damages the intestinal mucosa of the intestine, primarily the colon. Upon administration of a FOS/PHGG blend, fermentation of soluble fibers in the colon increases, resulting in an increase in the production of SCFA. Butyrate is the SCFA primarily produced by the fermentation of PHGG and it is well established that butyrate is the preferred fuel for the colonocytes, which require additional energy to restore and maintain function that has been damaged by IBD. By combining soluble fibers, there is a greater opportunity for the fibers to come in contact with a larger surface area in the colon and lengthen the fermentation time, allowing for higher quantities of butyrate to reach distal portions of the colon, primarily targeting tissue that has been damaged by ulcerative colitis. By combining FOS and PHGG, fibers that are soluble and are preferentially fermented by different bacteria, both butyrate production and prebiotic effect are increased.

The FOS/PHGG blend of the present invention is similarly beneficial for individuals with irritable bowel syndrome (IBS). PHGG aids gut motility, alleviating both constipation and diarrhea, hallmarks of the disease. FOS imparts a prebiotic effect, restoring a healthy balance of intestinal bacteria. This is highly beneficial, as many individuals with IBS have a higher prevalence of coliform bacteria, which may lead to any number of disorders associated with the disease.

Furthermore, the inclusion of a blend of soluble fibers in nutritional formulas may increase the production and secretion of glucagon-like peptide-2 (GLP-2). GLP-2 is a hormone specific to the gut and which increases enterocyte proliferation and differentiation, and also decreases enterocyte apoptosis. In addition, GLP-2 increases the localization and abundance of specific proteins in enterocytes to increase nutrient transport in the intestine. Soluble fibers, and specifically PHGG, are preferentially fermented to produce butyrate, the SCFA thought to act on the L cell (the cell that produces GLP-2) to increase the production and secretion of GLP-2.

GLP-2 is an important hormone in the reduction of intestinal inflammation. As such, fibers such as PHGG, which have the potential to preferentially increase GLP-2 production and/or secretion, have an anti-inflammatory effect on the intestinal tract.

Accordingly, a blend of FOS and PHGG according to the present invention is efficacious in alleviating symptoms associated with IBD and IBS, along with the potential treatment and/or prevention of these and other diseases and disorders, as described above.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to a person skilled in the art are intended to be included within the scope of the invention as defined by the accompanying claims.

What is claimed is:

1. A dietary fiber formulation comprising:
   a first soluble fiber comprising partially-hydrolyzed guar gum (PHGG); and
   a second soluble fiber comprising fructooligosaccharide (FOS), wherein the dietary fiber formulation exhibits a prebiotic potential greater than a prebiotic potential of the first soluble fiber and the second soluble fiber individually, and wherein the soluble fibers are included in the formulation in a ratio of FOS : PHGG of 2 to 1.

2. The dietary fiber formulation of claim 1, wherein the FOS is produced from at least one of the following: synthesis from sucrose, hydrolysis of inulin, extraction from chickory root, extraction from Jerusalem artichoke, and extraction from Agave.

3. The dietary fiber formulation of claim 1, wherein the prebiotic potential includes an ability to increase an intestinal population of at least one bacterial species selected from a group consisting of: bifidobacteria, lactobacilli, and *eubacteria*.

4. The dietary fiber formulation of claim 1, wherein the prebiotic potential includes an ability to decrease an intestinal population of at least one bacterial species selected from a group consisting of: *bacteriodes, Clostridia, Eschericia coli*, and sulphate-reducing bacteria.

5. The dietary fiber formulation of claim 1, wherein the prebiotic potential includes an ability to increase intestinal fermentation time.

6. The dietary fiber formulation of claim 1, wherein the prebiotic potential includes an ability to increase production of a short-chain fatty acid (SCFA).

7. The dietary fiber formulation of claim 6, wherein the SCFA includes at least one selected from the group consisting of: acetate, propionate, and butyrate.

8. The dietary fiber formulation of claim 1, further comprising a probiotic.

9. The dietary fiber formulation of claim 8, wherein the probiotic is selected from a group consisting of: bifidobacteria, lactobacilli, and *eubacteria*.

10. The dietary fiber formulation of claim 1, wherein the prebiotic potential includes the ability of a portion of at least one of the first soluble fiber and the second soluble fiber to pass unfermented to the mid colon.

11. The dietary fiber formulation of claim 10, wherein the prebiotic potential includes the ability of a portion of at least one of the first soluble fiber and the second soluble fiber to pass unfermented to the distal colon.

12. The dietary fiber formulation of claim 1, wherein the prebiotic potential includes the ability of at least one of the first soluble fiber and the second soluble fiber to contact a greater surface area of the colon than if the first soluble fiber and the second soluble fiber were ingested separately.

13. A method of treating an individual recovering from surgery with a dietary fiber formulation, the method comprising:
   administering to the individual an effective amount of a dietary fiber formulation comprising: a first soluble fiber comprising partially-hydrolyzed guar gum (PHGG); and a second soluble fiber comprising fructooligosaccharide (FOS), wherein the dietary fiber formulation exhibits a prebiotic potential greater than a prebiotic potential of the first soluble fiber and the second soluble fiber individually, and wherein the soluble fibers are included in the formulation in a ratio of FOS : PHGG of 2 to 1.

14. A method of treating an individual suffering from at least one of diabetes, hypertension, dyslipidemia, obesity, heart disease, or stroke, the method comprising:
   administering to the individual an effective amount of at least one soluble dietary fiber formulation comprising a first soluble fiber comprising partially-hydrolyzed guar gum (PHGG) and a second soluble fiber comprising fructooligosaccharide (FOS), wherein the dietary fiber formulation exhibits a prebiotic potential greater than a prebiotic potential of the first soluble fiber and the second soluble fiber individually, and wherein the soluble fibers are included in the formulation in a ratio of FOS : PHGG of 2 to 1.

* * * * *